US007592021B2

(12) United States Patent
Shankar et al.

(10) Patent No.: US 7,592,021 B2
(45) Date of Patent: Sep. 22, 2009

(54) BIOADHESIVE DELIVERY SYSTEM FOR TRANSMUCOSAL DELIVERY OF BENEFICIAL AGENTS

(75) Inventors: Gita Natarajan Shankar, Saratoga, CA (US); Rae Lyn Burke, San Francisco, CA (US)

(73) Assignee: SRI International, Menlo Park, CA (US)

( * ) Notice: Subject to any disclaimer, the term of this patent is extended or adjusted under 35 U.S.C. 154(b) by 0 days.

(21) Appl. No.: 11/242,680

(22) Filed: Oct. 3, 2005

(65) Prior Publication Data

US 2006/0115532 A1 Jun. 1, 2006

Related U.S. Application Data

(60) Provisional application No. 60/615,415, filed on Oct. 2, 2004.

(51) Int. Cl.
*A61K 9/00* (2006.01)

(52) U.S. Cl. ........................................................ 424/484

(58) Field of Classification Search ........................ None
See application file for complete search history.

(56) References Cited

U.S. PATENT DOCUMENTS

| | | | | |
|---|---|---|---|---|
| 6,063,055 | A * | 5/2000 | Epstein et al. | ................ 604/82 |
| 6,309,630 | B1 | 10/2001 | Patel et al. | |
| 2002/0025326 | A1 | 2/2002 | Blonder et al. | |
| 2003/0199426 | A1 | 10/2003 | Carrara et al. | |
| 2004/0146534 | A1 | 7/2004 | Glenn et al. | |

FOREIGN PATENT DOCUMENTS

| | | |
|---|---|---|
| EP | 0 551 626 | 7/1993 |
| EP | 1 332 764 | 8/2003 |

OTHER PUBLICATIONS

BASF Corporation Technical Bulletin—Pluronic Block Copolymer.*
BASF Corporation MSDS—Lutrol F127.*
Belshe et al., "The efficacy of live, attenuated, cold-adapted, trivalent, intranasal influenza virus vaccine in children," New Engl. J. Med. (1998) 338:1405-1412.
Brachman and Friedlander, "Anthrax," in Vaccines, 3rd Ed., Chap. 24, Plotkin and Orenstein, eds., Saunders Co., pp. 629-637, 1999.
Cano et al., "Partial protection to respiratory syncytial virus (RSV) elicited in mice by intranasal immunization using live staphylococci with surface-displayed RSV-peptides," Vaccine (2000) 18:2743-2752.
Dyer et al., "Nasal delivery of insulin using novel chitosan based formulations: a comparative study in two animal models between simple chitosan formulations and chitosan nanoparticles," Pharm. Res. (2002) 19:998-1008.
Fitzgerald and Mrsny, "New approaches to antigen delivery," Crit. Rev. Therapeutic Drug Carrier Sys. (2000) 17:165-248.

Flick-Smith et al., "Mucosal or parenteral administration of microsphere-associated Bacillus anthracis protective antigen protects against anthrax infection in mice," Infect. Immun. (2002) 70:2022-2028.

Friedlander, "Anthrax" in Medical Aspects of Chemical and Biological Warfare, Chap. 22, Sidell, Takafuji, Franz, eds., Office of the Surgeon General, U.S. Department of the Army, Washington, DC, pp. 467-478, 1989.

Illum, "Nasal drug delivery—possibilities, problems and solutions," J. Controlled Release (2003) 87:187-198.

Illum et al., "Chitosan as a novel nasal delivery system for vaccines," Adv. Drug Deliv. Rev. (2001) 51:81-96.

Illum, "Bioadhesive formulations for nasal peptide delivery," in Drug Delivery—Issues in Fundamentals, Novel Approaches and Development, Chap. 19, Lehr and Chickering, eds, Marcel Dekker, New York, pp. 507-539, 1998.

Kabanov et al., "Pluronic® block copolymers as novel polymer therapeutics for drug and gene delivery," J. Controlled Release (2002) 82:189-212.

Leppla, "Anthrax Toxins," in Bacterial Toxins and Virulence Factors in Disease, vol. 8, Chap. 23, Moss et al., eds., Marcel Dekker, New York, pp. 543-572, 1995.

Matsuo et al., "Induction of innate immunity by nasal influenza vaccine administered in combination with an adjuvant (cholera toxin)," Vaccine (2000) 18:2713-2722.

Pandy A et al., "Effect of additives on the clouding behavior of an ethylene oxide-propylene oxide block copolymer in aqueous solution," J. Macromol. Sci—Pure Appl. Chem. (1993) 30:1-18.

Schmolka, "A comparison of block copolymer surfactant gels," J. Am. Oil Chem. Soc. (1991) 68:206-209.

(Continued)

*Primary Examiner*—Robert B Mondesi
*Assistant Examiner*—Brian J Gangle
(74) *Attorney, Agent, or Firm*—Richard Aron Osman

(57) ABSTRACT

Formulations and methods for transmucosal delivery of a beneficial agent are described in which a pH-responsive component and a temperature-responsive component are combined and applied to a mucous membrane. The temperature-responsive component is a component that, in aqueous solutions, is capable of undergoing a temperature-dependent sol to gel phase transition. The formulations may be characterized as having bioadhesive properties, and are suitable for delivery of a variety of beneficial agents.

100 Claims, 4 Drawing Sheets

OTHER PUBLICATIONS

Scholes et al., "Detection and determination of surface levels of poloxamer and PVA surfactant on biodegradable nanospheres using SSIMS and XPS," J. Controlled Release (1999) 59:261-278.

Vermani et al., "Assemblies for in vitro measurement of bioadhesive strength and retention characteristics in simulated vaginal environment," Drug Dev. Indus. Pharm. (2002) 28:1133-1146.

Westerink et al., "Projuvant™ (Pluronic F127® /chitosan) enhances the immune response to intranasally administered tetanus toxoid," Vaccine (2002) 20:711-723.

Tirnaksiz et al., "Rheological, mucoadhesive and release properties of Pluronic F-127 gel and Pluronic F-127/polycarbophil mixed gel systems," Pharmazie (2005) 60:518-523.

Yun et al., "Prolonged antifungal effects of clotrimazole-containing mucoadhesive thermosensitive gels on vaginitis," J. Controlled Rel. (2002) 82:39-50.

Noveon Company Technical Literature, "Bulletin 12: Flow and Suspension Properties," Jan. 2002.

* cited by examiner

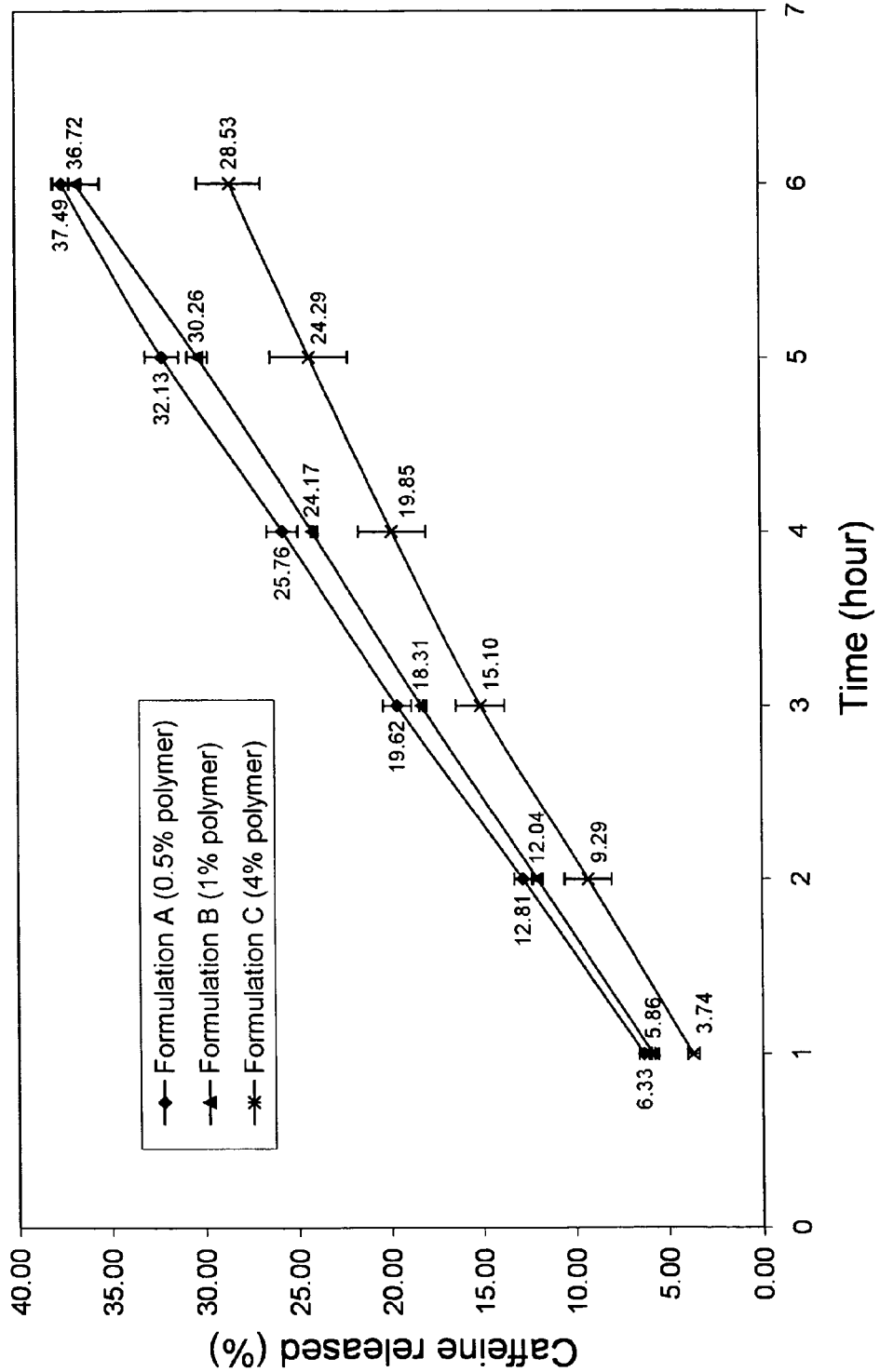

BIOADHESIVE DELIVERY SYSTEM FOR TRANSMUCOSAL DELIVERY OF BENEFICIAL AGENTS

CROSS REFERENCE TO RELATED APPLICATION

This application claims priority under 35 U.S.C. § 119(e)(1) to Provisional U.S. Patent Application Ser. No. 60/615,415, filed Oct. 2, 2004, which is incorporated herein by reference in its entirety.

GOVERNMENT RIGHTS

This invention was made with Government support under contract Number 1 R03 AI59234-01 awarded by the National Institute of Allergy and Infectious Disease. The Government has certain rights in this invention.

TECHNICAL FIELD

The present invention relates to formulations and methods for transmucosal delivery of beneficial agents. More specifically, the invention relates to bioadhesive, multi-component formulations and methods of administration that allow for sustained and/or enhanced release of beneficial agents via mucous membranes.

BACKGROUND

Transmucosal delivery has many advantages as a method for the administration of beneficial agents. Because of the potential to achieve both a systemic and localized effect, e.g., a systemic and local immune response, transmucosal administration is attractive for its ability to be tailored to the needs of a particular beneficial regimen. The rapid onset of therapeutic action can be advantageous, and mucociliary activity results in faster clearance of medication, thus increasing the bioavailability of the beneficial agent. Compared with other routes, administration of large molecules such as proteins and peptides is rapid and efficient. Transmucosal delivery involves relatively simple, low cost methods of application such as aerosols and liquids that can be delivered via nebulizers, bottles, applicators and syringes. Ease of administration often results in improved patient compliance as compared with intravenous delivery.

Many types of active agents have been evaluated as candidates for transmucosal administration. The mucous membrane of the nasal cavity is frequently used for the delivery of anti-allergens as well as medications useful in the treatment of localized infections. More recently, the nasal route has been exploited for the delivery of anti-migraine drugs, peptides useful in the treatment of osteoporosis, diabetes, prostate cancer, and vaccines.

The mucous membranes are an ideal location for the introduction of vaccines. Successful use of a vaccine, which may consist of preparations of weakened or dead pathogens, requires an immune system response in order to elicit protection against infection. Because they are the primary site of many pathogen-host encounters, mucous membranes are characterized by a strong immune system response to foreign material. In addition, the mucous membrane often represents a relatively hospitable environment for pathogens and antigens alike.

Many prophylactic and treatment regimes require numerous intramuscular (IM) or subcutaneous (SC) injections of antigens. As an example, currently there are two commercially available anthrax vaccines and five recombinant subunit PA (Protective Antigen) vaccines in development. A vaccine licensed for human use in the United Kingdom contains PA from *Bacillus anthracis* filtrate precipitated with alum; it requires four IM doses in a six-month period. A vaccine licensed for use in humans in the United States is Anthrax Vaccine Adsorbed (AVA), which employs aluminum-hydroxide adsorbed PA from the culture supernatant of a specific *B. anthracis* strain. AVA requires six subcutaneous doses in 18 months (at 0, 2, and 4 weeks and 6, 12, and 18 months) and subsequent yearly boosters. It gives reasonable protection against inhalation anthrax but is reputed to cause adverse effects in some individuals. AVA contains 50 μg protein per dose, as well as aluminum hydroxide (0.65 mg aluminum/dose) as adjuvant, benzethonium chloride (0.0025%) as a preservative, and formaldehyde (0.01%) as stabilizer. Both of these commercially available vaccines can cause local reactions.

Chitosan, a derivative of the natural polymer chitin, has been investigated as a bioadhesive material and as an adjuvant in transmucosal delivery systems. Unfortunately, the use of effective amounts of chitosan can result in highly viscous formulations. Furthermore, chitosan is insoluble in aqueous solutions with a pH above 6.5. Since the pH in the nasal mucosa is approximately 7, formulations containing chitosan may lose potency when applied to the nasal mucosa.

Accordingly, there remains a need in the art for improved formulations, systems, and methods for transmucosal administration of beneficial agents. Ideally, a transmucosal delivery system would (1) provide for sustained release of any of a variety of beneficial agents, (2) be capable of placement on and delivery across different mucosal surfaces of the body, (3) allow control over the length of the time period during which active agent delivery takes place, and (4) provide rapid onset of action and increased bioavailability. An optimal transmucosal delivery system for administration of vaccines should also provide for an enhanced immune response and an increase in efficacy.

BRIEF DESCRIPTION OF THE INVENTION

The present invention is directed to the aforementioned need in the art, and, in one embodiment, provides a pharmaceutical formulation for transmucosal delivery of a beneficial agent, wherein the pharmaceutical formulation comprises: a pH-responsive compound; a temperature-responsive compound that in an aqueous medium is capable of undergoing a temperature-dependent sol to gel phase transition; a base; an effective amount of a beneficial agent; and water.

In another embodiment, the invention provides a pharmaceutical formulation for mucosal administration of a beneficial agent comprising a pH-responsive compound and a temperature-responsive compound. The pH-responsive compound is a polymer that is bioadhesive and lightly crosslinked, and the temperature-responsive compound is capable in aqueous solutions of undergoing a temperature-responsive sol to gel phase transition.

In yet another embodiment, the invention provides a method for treating a patient afflicted with from a bacterial infection, wherein the method comprises administering to the patient a therapeutically effective amount of a pharmaceutical formulation comprising: a pH-responsive compound; a temperature-responsive compound; a base; water; and an effective amount of a therapeutic agent. The temperature responsive compound is a compound that in an aqueous medium is capable of undergoing a temperature-responsive phase transition from sol to gel. The pharmaceutical formulation is administered via application to a mucous membrane.

In a further embodiment, the invention provides a method for decreasing the likelihood of a bacterial infection occurring in a patient, wherein the method comprises administering to the patient an effective amount of a pharmaceutical formulation comprising: a pH-responsive compound; a temperature-responsive compound; a base; water; and a prophylactically effective amount of a beneficial agent. The pharmaceutical formulation is administered via application to a mucous membrane. The temperature-responsive compound is a compound that in an aqueous medium is capable of a temperature-responsive phase transition from sol to gel.

In a still further embodiment, the invention provides for a method for delivering a beneficial agent into a mucous membrane of a patient, wherein the method comprises applying to the mucous membrane a pharmaceutical formulation. The pharmaceutical formulation comprises: a first component comprising a pH-responsive compound; a second component comprising a base and a temperature-responsive compound; and an effective amount of a beneficial agent. The temperature-responsive compound is a compound that in an aqueous medium is capable of undergoing a temperature-responsive sol to gel phase transition.

In another embodiment, the invention provides for a prophylactic kit for reducing the likelihood of a bacterial infection in a patient, wherein the prophylactic kit comprises a pharmaceutical formulation and a means for delivery of the pharmaceutical formulation. The pharmaceutical formulation comprises: a pH-responsive compound; a temperature-responsive compound that in an aqueous medium is capable of undergoing a temperature-responsive sol to gel phase transition; a base; a prophylactically effective amount of a beneficial agent; and water.

In a still further embodiment, a kit is provided for treating a bacterial infection in a patient, wherein the treatment kit comprises a pharmaceutical formulation and a means for delivery of the pharmaceutical formulation. The pharmaceutical formulation comprises: a pH-responsive compound; a temperature-responsive compound that in an aqueous medium is capable of undergoing a temperature-responsive sol to gel phase transition; a base; an effective amount of a therapeutic agent; and water.

BRIEF DESCRIPTION OF THE DRAWINGS

FIG. 4 is a graph displaying the percentage of caffeine released into phosphate buffered solution from gels of different composition.

DETAILED DESCRIPTION OF THE INVENTION

Definitions and Nomenclature

Figure 1:
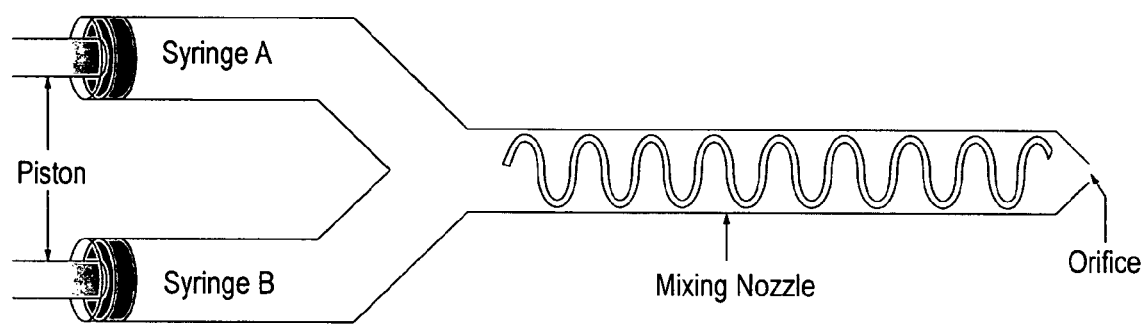
FIG. 1 is a drawing of a double-barreled applicator with a mixing nozzle suitable for administration of the formulations of the invention.

Unless otherwise indicated, the invention is not limited to specific formulations, administration regimens, drug delivery devices, or the like, as such may vary. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Thus, for example, reference to "an active agent" includes not only a single active agent but also a combination or mixture of two or more different active agents, reference to "a polymer" includes a single polymer as well as two or more polymers in combination or admixture, and the like.

As used herein, the terms "may," "optionally," and "may optionally" are used interchangeably and are meant to include cases in which the condition occurs as well as cases in which the condition does not occur. Thus, for example, the statement that a formulation "may include an excipient" is meant to include cases in which the formulation includes an excipient as well as cases in which the formulation does not include an excipient.

In describing and claiming the present invention, the following terminology will be used in accordance with the definitions set out below.

The terms "beneficial agent" and "active agent" are used interchangeably herein to refer to a chemical compound or composition that has a beneficial biological effect. Beneficial biological effects include both therapeutic effects, i.e., treatment of a disorder or other undesirable physiological condition, and prophylactic effects, i.e., prevention of a disorder or other undesirable physiological condition (e.g., pregnancy). The terms also encompass pharmaceutically acceptable, pharmacologically active derivatives of beneficial agents specifically mentioned herein, including, but not limited to, salts, esters, amides, prodrugs, active metabolites, isomers, fragments, analogs, and the like. When the terms "beneficial agent" or "active agent" are used, then, or when a particular agent is specifically identified, it is to be understood that the term includes the agent per se as well as pharmaceutically acceptable, pharmacologically active salts, esters, amides, prodrugs, conjugates, active metabolites, isomers, fragments, analogs, etc.

Unless otherwise indicated, the terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. "Preventing" a disorder or unwanted physiological event in a patient refers specifically to the prevention of the occurrence of symptoms and/or their underlying cause, wherein the patient may or may not exhibit heightened susceptibility to the disorder or event.

By the term "effective amount" of a therapeutic agent is meant a nontoxic but sufficient amount of a beneficial agent to provide the desired effect. The amount of beneficial agent that is "effective" will vary from subject to subject, depending on the age and general condition of the individual, the particular beneficial agent or agents, and the like. Thus, it is not always possible to specify an exact "effective amount." However, an appropriate "effective" amount in any individual case may be determined by one of ordinary skill in the art using routine experimentation.

As used herein, and unless specifically stated otherwise, an "effective amount" of a beneficial refers to an amount covering both therapeutically effective amounts and prophylactically effective amounts.

As used herein, a "therapeutically effective amount" of an active agent refers to an amount that is effective to achieve a desired therapeutic result, and a "prophylactically effective amount" of an active agent refers to an amount that is effective to prevent an unwanted physiological condition. Therapeutically effective and prophylactically effective amounts of a given active agent will typically vary with respect to factors such as the type and severity of the disorder or disease being treated and the age, gender, and weight of the patient.

By a "pharmaceutically acceptable" component is meant a component that is not biologically or otherwise undesirable, i.e., the component may be incorporated into a pharmaceutical formulation of the invention and administered to a patient as described herein without causing any significant undesirable biological effects or interacting in a deleterious manner with any of the other components of the formulation in which it is contained. When the term "pharmaceutically acceptable" is used to refer to an excipient, it is generally implied that the component has met the required standards of toxicological and manufacturing testing or that it is included on the Inactive Ingredient Guide prepared by the U.S. Food and Drug Administration.

The term "pharmacologically active" (or simply "active"), as in a "pharmacologically active" derivative or analog, refers to a derivative or analog (e.g., a salt, ester, amide, conjugate, metabolite, isomer, fragment, etc.) having the same type of pharmacological activity as the parent compound and approximately equivalent in degree.

The term "controlled release" refers to a formulation, dosage form, or region thereof from which release of a beneficial agent is not immediate, i.e., with a "controlled release" dosage form, administration does not result in immediate release of the beneficial agent in an absorption pool. The term is used interchangeably with "nonimmediate release" as defined in Remington: *The Science and Practice of pharmacy*, Nineteenth Ed. (Easton, Pa.: Mack Publishing Company, 1995). In general, the term "controlled release" as used herein includes sustained release and delayed release formulations.

The term "sustained release" (synonymous with "extended release") is used in its conventional sense to refer to a formulation, dosage form, or region thereof that provides for gradual release of a beneficial agent over an extended period of time, and that preferably, although not necessarily, results in substantially constant blood levels of the agent over an extended time period.

The term "ionizable" refers to a compound containing at least one functional group that (a) bears a positive or negative charge (i.e., is "ionized") and is therefore associated with a counterion of opposite charge, or (b) is electronically neutral but ionized at a higher or lower pH. Thus, ionizable compounds include quaternary ammonium salts as well as uncharged amines, and carboxylate moieties as well as uncharged carboxyl groups.

The term "naturally occurring" refers to a compound or composition that occurs in nature, regardless of whether the compound or composition has been isolated from a natural source or chemically synthesized.

The term "polymer" as used herein refers to a molecule containing a plurality of covalently attached monomer units, and includes branched, dendrimeric and star polymers as well as linear polymers. The term also includes both homopolymers and copolymers, e.g., random copolymers, block copolymers and graft copolymers, as well as uncrosslinked polymers and slightly to moderately to substantially crosslinked polymers.

The term "mixture" as used herein is meant to include solutions in which the components of the mixture are completely miscible, as well as suspensions and emulsions, in which the components of the mixture are not completely miscible.

The term "crosslink" as used herein is meant to refer to both chemical (i.e., covalent) and non-chemical crosslinks. Non-chemical crosslinks may be, by way of example and not limitation, ionic bonds and hydrogen bonds.

The term "gel" as used herein refers to that portion of a compound that is insoluble in all solvents at elevated temperatures under conditions where polymer degradation does not occur. The term "sol" as used herein refers to that portion of a compound that is soluble in a solvent or solvents. Thus, a "sol-gel transition" is understood to occur when a portion of a compound becomes insoluble due to crosslinking.

When referring to diseases, it is understood that unless otherwise stated, the reference is meant to include any of the family of diseases that may be associated with the name. For example, reference to "anthrax" is meant to include the cutaneous, gastrointestinal and pulmonary types of anthrax infections.

Unless otherwise stated, viscosity values have units of centipoise (cp), and are reported as measured on a Brookfield viscometer (model DV-II+, Brookfield Engineering Labs, Middleboro, Mass.) at ambient temperature (i.e., about 25° C.) with a CPE-41 HBDV-II+ cone spindle and at a shear rate of 0.6 revolutions per minute (rpm). The spindle is allowed to make five revolutions before a measurement is taken.

II. Formulation Components

The present invention provides for pharmaceutical formulations for transmucosal delivery of a beneficial agent comprising a pH-responsive component and a temperature-responsive component.

A. The pH-responsive Component

The pH-responsive component may be a compound or combination of compounds. Preferably, the pH-responsive component is a compound that forms aqueous mixtures wherein the viscosity of the mixture is dependent upon pH. Preferred pH-responsive compounds are classified as GRAS (Generally Recognized as Safe) and can be obtained from commercial sources. The compounds may also be synthesized prior to use using techniques that are well-established in the art.

Preferred pH-responsive compounds are polyionic, meaning that they comprise a plurality of ionizable groups. The ionized form of the ionizable groups may be either cationic or anionic, or any combination thereof. Particularly preferred pH-responsive compounds are polymers. The polymer may be either polyanionic or polycationic, such that aqueous mixtures of the polymer may be either acidic or basic, respectively. The pH-responsive polymer may also be neutral, and contain groups that are capable of being converted to ionizable groups.

The pH-responsive compounds may be either water-soluble or water-insoluble. Particularly preferred polymers that function as pH-responsive compounds are lightly crosslinked. By "lightly crosslinked" is meant that chemical (i.e., covalent) crosslinks exist between polymer chains, but that the crosslink density is low enough that aqueous suspensions of the polymer can be either homogeneous or nearly homogeneous.

Preferably, polymers that function as pH-responsive compounds are shear thinning. As discussed below, a preferred method of delivery of the formulations of the invention is via a nebulizer. Shear thinning is a property of the pH-responsive compound that allows for aerosolization of the formulations.

The pH-responsive compound is most preferably a polyanionic polymer. By "polyanionic polymer" is meant a polymer that contains a plurality of anionic groups, or groups that are capable of being converted to anionic groups. This includes polymers containing attached carboxylate groups or carbonyl-containing groups such as ester groups. The polyanionic polymer may be in the form of a solid, or it may be in the form of a solution comprising a solvent. It is to be understood that polyanionic polymers may be associated with a variety of cationic counterions. Examples of polyanionic polymers include homopolymers and copolymers of acrylic acid and/or acrylic acid derivatives.

The pH-responsive compound may be obtained from commercial sources and used as supplied, or it may be synthesized specifically for the formulations of the invention.

Particularly preferred pH-responsive polymers are selected from polycarbophils, with NOVEON® AA-1 being most preferred. Polycarbophil is the generic name of a family of homopolymers of acrylic acid marketed by Noveon, Inc. (Cleveland, OH). Polycarbophil polymers are designed to mimic negatively charged mucin, the glycoprotein component of mucus that is responsible for the attachment of mucus to underlying epithelial surfaces. Polycarbophils are lightly crosslinked polymers, prepared using divinyl glycol as the crosslinking agent. Polycarbophils are shear thinning, and combinations of polycarbophil with water provide homogeneous or nearly homogeneous mixtures with a pH that is dependent upon the amount of polycarbophil. For example, a mixture of water and 2 wt % NOVEON® AA-1 has a pH of about 3.5. Mixtures of polycarbophil, in the absence of added base, remain in the free-flowing form during storage at a wide range of temperatures. An important factor for controlling the viscosity of a polycarbophil formulation is the addition of base ions to regulate the pH of the solution. Alkali added to the formulation ionizes the carboxylic acid backbone, allowing for hydrogen bonds with water as well as with mucosa (thereby imparting bioadhesive properties to mixtures containing polycarbophils).

In the formulations of the invention, the amount of pH-responsive compound is in the range of about 0.5% to about 10%, more preferably about 1% to about 5% of the formulation by weight.

B. The Temperature-responsive Component

The temperature-responsive component may be a compound or combination of compounds. Preferably, the temperature-responsive component is a compound that, in aqueous medium, e.g., in an aqueous solution, is capable of undergoing a sol-gel phase transition in response to changes in temperature. It is to be appreciated that the nature of the sol-gel phase transition will be dependent upon a variety of factors. In particular, for any temperature-responsive compound, the sol-gel phase transition temperature will be dependent upon the concentration of the compound.

Temperature-responsive compounds useful in the invention exhibit the property of thermosensitive gelation. Such compounds preferably exhibit reverse thermal gelation. When a compound exhibits reverse thermal gelation, at one temperature the compound is water soluble, and at a higher temperature the compound forms an insoluble gel.

In the formulations of the invention, the amount of temperature-responsive compound is preferably in the range of about 0.5% to about 10%, more preferably about 1% to about 5% of the formulation by weight. It is preferred that the sum of the weight of the temperature-responsive compound and the weight of the pH-responsive compound be in the range of about 1% to about 10% of the formulation by weight, more preferably about 2% to about 5% by weight, and most preferably about 4% by weight, wherein a preferred formulation comprises 2 wt % of the pH-responsive compound and 2 wt % of the temperature-responsive compound.

Preferred temperature-responsive compounds are polymers, with block copolymers that are capable of forming micelles in aqueous media, e.g., in aqueous solutions, being particularly preferred.

Preferred temperature-responsive compounds are selected from the group of poloxamers known as PLURONICS®. PLURONICS® are low molecular weight triblock copolymers of poly(ethylene oxide)(PEO) and poly(propylene oxide)(PPO). The absolute and relative sizes of the PEO and PPO blocks can be varied over a wide spectrum, allowing for the preparation of compounds with a variety of properties. As a result, numerous PLURONIC® compositions are available and suitable for the formulations of the invention, with PLURONIC® F127 being most preferred.

The presence of the temperature-responsive compound in the formulations of the invention commonly imparts a "pseudo sol-gel phase transition temperature," or "formulation sol-gel phase transition temperature" to the formulations. By "formulation sol-gel phase transition temperature" is meant that the formulation may contain insoluble portions, even in the sol phase. However, the formulation continues to be free-flowing until the formulation sol-gel phase transition temperature is exceeded. This transition temperature is dependent upon a number of factors, including the amounts and identities of the temperature-responsive and pH-responsive compounds, pH, and the presence of additives such as salts and fillers. It is preferable that the formulation sol-gel phase transition temperature is in the range of about 25° C. to about 40° C., more preferably about 30° C. to about 40° C.

C. Bases

The formulations of the invention may contain an added base. The identity and concentration of the base is preferably selected to affect the viscosity of the formulation. In particular, and without wishing to be bound by theory, when the pH-responsive compound is a polyanionic polymer, the polyanionic polymer is ionized (or further ionized) when combined with base. Ionization allows the polymer to form more extensive hydrogels, which are essentially hydrogen-bonding networks involving the polymer and water. This increase in the extent of gelation causes an increase in the viscosity of the mixture.

When polycarbophil is used as the pH-responsive compound, suitable bases include without limitation monovalent hydroxides and organic amines. Examples include sodium hydroxide, potassium hydroxide, ammonium hydroxide, triethanolamine, aminomethyl propanol, 2-amino-2-hydroxymethyl-1,3-propanediol, and tetrahydroxypropyl ethylenediamine.

The viscosities of the formulations of the invention are determined by a variety of factors. Viscosities may be particularly dependent upon pH. Preferably, the amount of the base will be chosen such that the pH of the formulation is in the range of about 4 to about 8, more preferably about 5 to about 7, and most preferably about 5.5 to about 7. As a further guide, the amount of the base is chosen such that, when applied to a mucous membrane at physiological temperatures, the viscosity of the formulation is between about 40,000 centipoise and about 300,000 centipoise, more preferably between about 70,000 centipoise and about 120,000 centipoise.

D. Beneficial Agents

The beneficial agent may be any prophylactic agent or therapeutic agent suitable for mucosal administration. The beneficial agent may be selected to achieve either a local or a systemic response. Suitable beneficial include without limitation analgesics and analgesic combinations, anesthetics, anorexics, anti-allergics, antiarthritics, antiasthmatic agents, antibiotics, anticholinergics, anticonvulsants, antidepressants, antidiabetic agents, antidiarrheals, antifungals, antigens, antihistamines, antihypertensives, antiinflammatories, antimigraine preparations, antinauseants, antineoplastics, antiparkinsonism drugs, antiprotozoans, antipruritics, antipsychotics, antipyretics, antispasmodics, antivirals, calcium channel blockers, cardiovascular preparations, central nervous system stimulants, contraceptives, cough and cold preparations including decongestants, diuretics, enzyme inhibitors, enzymes, genetic material including DNA and RNA, growth factors, growth hormones, hormone inhibitors, hypnotics, immunoactive agents, immunosuppressive agents, microbicides, muscle relaxants, parasympatholytics, peptides, peripheral and cerebral vasodilators, proteins, psychostimulants, receptor agonists, sedatives, spermicides and other contraceptives, steroids, sympathomimetics, tranquilizers, vaccines, vasodilating agents including general coronary, viral vectors, small organic molecules, and combinations thereof.

Suitable vaccines include vaccines that lower the likelihood of bacterial infections and diseases such as anthrax, tuberculosis, cholera, *haemophilus influenzae* type b, meningitis, *pertussis*, plague, infections and diseases causing pneumonia (such as infection by *Streptococcus pneumoniae*), typhoid and *staphylococcus aureus*. Suitable vaccines also include vaccines that lower the likelihood of viral infections and diseases, such as hepatitis B, influenza, measles, mumps, poliovirus, rabies, rubella, and yellow fever. Examples of vaccines for these infections and diseases are described by A. Gennaro, *Remington's Pharmaceutical Sciences*, 18$^{th}$ Edition (Easton: Mack Publishing, 1990), Chapter 72, the contents of which is herein incorporated by reference.

Preferred vaccines are those directed at reducing the likelihood of anthrax infections, such as those that contain protective antigens (PAs). Examples include vaccines that contain PAs from *Bacillus anthracis* filtrate precipitated with alum, and Anthrax Vaccine Adsorbed (AVA), which employs aluminum-hydroxide adsorbed PA from the culture supernatant of a specific *Bacillus anthracis* strain.

Antiviral agents include nucleoside phosphonates and other nucleoside analogs, AICAR (5-amino-4-imidazolecarboxamide ribonucleotide) analogs, glycolytic pathway inhibitors, anionic polymers, and the like, more specifically: antiherpes agents such as acyclovir, famciclovir, foscarnet, ganciclovir, idoxuridine, sorivudine, trifluridine, valacyclovir, and vidarabine; and other antiviral agents such as abacavir, adefovir, amantadine, amprenavir, cidofovir, delviridine, 2-deoxyglucose, dextran sulfate, didanosine, efavirenz, indinavir, interferon alpha, lamivudine, nelfinavir, nevirapine, ribavirin, rimantadine, ritonavir, saquinavir, squalamine, stavudine, tipranavir, valganciclovir, zalcitabine, zidovudine, zintevir, and mixtures thereof. Still other antiviral agents are glycerides, particularly monoglycerides, that have antiviral activity. One such agent is monolaurin, the monoglyceride of lauric acid.

Anti-inflammatory agents include corticosteroids, e.g., lower potency corticosteroids such as hydrocortisone, hydrocortisone-21-monoesters (e.g., hydrocortisone-21-acetate, hydrocortisone-21-butyrate, hydrocortisone-21-propionate, hydrocortisone-21-valerate, etc.), hydrocortisone-17,21-diesters (e.g., hydrocortisone-17,21-diacetate, hydrocortisone-17-acetate-21-butyrate, hydrocortisone-17,21-dibutyrate, etc.), alclometasone, dexamethasone, flumethasone, prednisolone, or methylprednisolone, or higher potency corticosteroids such as clobetasol propionate, betamethasone benzoate, betamethasone diproprionate, diflorasone diacetate, fluocinonide, mometasone furoate, triamcinolone acetonide, and mixtures thereof.

Local anesthetic agents include acetamidoeugenol, alfadolone acetate, alfaxalone, amucaine, amolanone, amylocalne, benoxinate, benzocaine, betoxycaine, biphenamine, bupivacaine, burethamine, butacaine, butaben, butanilicaine, buthalital, butoxycaine, carticaine, 2-chloroprocaine, cocaethylene, cocaine, cyclomethycaine, dibucaine, dimethisoquin, dimethocaine, diperadon, dyclonine, ecgonidine, ecgonine, ethyl aminobenzoate, ethyl chloride, etidocaine, etoxadrol, β-eucaine, euprocin, fenalcomine, fomocaine, hexobarbital, hexylcaine, hydroxydione, hydroxyprocaine, hydroxytetracaine, isobutyl p-aminobenzoate, ketamine, leucinocaine mesylate, levobupivacaine, levoxadrol, lidocaine, mepivacaine, meprylcaine, metabutoxycaine, methohexital, methyl chloride, midazolam, myrtecaine, naepaine, octacaine, orthocaine, oxethazaine, parethoxycaine, phenacaine, phencyclidine, phenol, piperocaine, piridocaine, polidocanol, pramoxine, prilocalne, procaine, propanidid, propanocaine, proparacaine, propipocaine, propofol, propoxycaine, pseudococaine, pyrrocaine, risocaine, salicyl alcohol, tetracaine, thialbarbital, thimylal, thiobutabarbital, thiopental, tolycaine, trimecaine, zolamine, phenol, and mixtures thereof.

Antibiotic agents include those of the lincomycin family, such as lincomycin per se, clindamycin, and the 7-deoxy,7-chloro derivative of lincomycin (i.e., 7-chloro-6,7,8-trideoxy-6-[[(1-methyl-4-propyl-2-pyrrolidinyl)carbonyl]amino]-1-thio-L-threo-α-D-galacto-octopyranoside); other macrolide, aminoglycoside, and glycopeptide antibiotics such as erythromycin, clarithromycin, azithromycin, streptomycin, gentamicin, tobramycin, amikacin, neomycin, vancomycin, and teicoplanin; antibiotics of the tetracycline family, including tetracycline per se, chlortetracycline, oxytetracycline, demeclocycline, rolitetracycline, methacycline and doxycycline; and sulfur-based antibiotics, such as the sulfonamides sulfacetamide, sulfabenzamide, sulfadiazine, sulfadoxine, sulfamerazine, sulfamethazine, sulfamethizole, and sulfamethoxazole; streptogramin antibiotics such as quinupristin and dalfopristin; and quinolone antibiotics such as ciprofloxacin, nalidixic acid, ofloxacin, and mixtures thereof.

Antifungal agents include miconazole, terconazole, isoconazole, itraconazole, fenticonazole, fluconazole, ketoconazole, clotrimazole, butoconazole, econazole, metronidazole, 5-fluorouracil, amphotericin B, and mixtures thereof.

Other anti-infective agents include miscellaneous antibacterial agents such as chloramphenicol, spectinomycin, polymyxin B (colistin), and bacitracin, anti-mycobacterials such as such as isoniazid, rifampin, rifabutin, ethambutol, pyrazinamide, ethionamide, aminosalicylic acid, and cycloserine, and antihelminthic agents such as albendazole, oxfendazole, thiabendazole, and mixtures thereof.

Steroids include androgens, estrogens, and progestins. Examples of suitable androgenic agents that may be used in the formulations of the present invention include, but are not limited to: the naturally occurring androgens and derivatives thereof, including androsterone, androsterone acetate, androsterone propionate, androsterone benzoate, androstenediol, androstenediol-3-acetate, androstenediol-17-acetate, androstenediol-3,17-diacetate, androstenediol-17-benzoate, androstenediol-3-acetate-17-benzoate, androstenedione, dehydroepiandrosterone (DHEA; also termed "prasterone"), sodium dehydroepiandrosterone sulfate, 5α-dihydrotestosterone, dromostanolone, dromostanolone propionate, ethylestrenol, nandrolone phenpropionate, oxandrolone, stanozolol and testosterone; pharmaceutically acceptable esters of testosterone and 4-dihydrotestosterone, typically esters formed from the hydroxyl group present at the C-17 position, including, but not limited to, the enanthate, propionate, cypionate, phenylacetate, acetate, isobutyrate, buciclate, heptanoate, decanoate, undecanoate, caprate and isocaprate esters; and pharmaceutically acceptable derivatives of testosterone such as methyl testosterone, testolactone, oxymetholone and fluoxymesterone. Testosterone and testosterone esters, such as testosterone enanthate, testosterone propionate and testosterone cypionate, are particularly preferred androgenic agents for use in conjunction with the present invention. The aforementioned testosterone esters are commercially available or may be readily prepared using techniques known to those skilled in the art or described in the pertinent literature. (Generally, the 17-hydroxyl group of the testosterone molecule is caused to react with a suitable organic acid under esterifying conditions, such conditions typically involving the use of a strong acid such as sulfuric acid, hydrochloric acid, or the like, and a temperature sufficient to allow the reaction to proceed at reflux.)

Suitable estrogens that may be administered using the formulations of the invention include without limitation synthetic and natural estrogens such as: estradiol (i.e., 1,3,5-estratriene-3,17β-diol, or "β-estradiol") and its esters, including estradiol benzoate, valerate, cypionate, heptanoate, decanoate, acetate and diacetate; 17α-estradiol; ethynylestradiol (i.e., 17α-ethynylestradiol) and esters and ethers thereof, including ethynylestradiol 3-acetate and ethynylestradiol 3-benzoate; estriol and estriol succinate; polyestrol phosphate; estrone and its esters and derivatives, including estrone acetate, estrone sulfate, and piperazine estrone sulfate; quinestrol; mestranol; and conjugated equine estrogens. Estradiol and ethynylestradiol are particularly preferred synthetic estrogenic agents for use in conjunction with the present invention.

Suitable progestins for use in the formulations of the invention include, but are not limited to, acetoxypregnenolone, allylestrenol, anagestone acetate, chlormadinone acetate, cyproterone, cyproterone acetate, desogestrel, dihydrogesterone, dimethisterone, ethisterone (17α-ethynyltestosterone), ethynodiol diacetate, flurogestone acetate, gestadene, hydroxyprogesterone, hydroxyprogesterone acetate, hydroxyprogesterone caproate, hydroxymethylprogesterone, hydroxymethylprogesterone acetate, 3-ketodesogestrel, levonorgestrel, lynestrenol, medrogestone, medroxyprogesterone acetate, megestrol, megestrol acetate, melengestrol acetate, norethindrone, norethindrone acetate, norethisterone, norethisterone acetate, norethynodrel, norgestimate, norgestrel, norgestrienone, normethisterone, and progesterone. Progesterone, cyproterone acetate, norethindrone, norethindrone acetate and levonorgestrel are preferred progestins.

Other beneficial agents include, without limitation, enzyme inhibitors such as sildenafil citrate, hormone inhibitors such as dopamine, and contraceptives such as nonoxynol-9, octoxynol-8, benzalkonium chloride, and sodium cholate. Still other beneficial agents include sumatriptan, sumatriptan succinate, zolmitriptan, calcitonin, calcitonin-salmon, cyanocobalamin, beclomethasone, beclomethasone dipropionate, fluticasone, fluticasone propionate, triamcinolone, triamcinolone acetonide, flunisolide, mometasone furoate, mometasone furoate monohydrate, budesonide, butorphanol, desmopressin, dihydroergotamine, isoproterenol, nitroglycerin, naferelin acetate, oxytocin, zanamivir, and nicotine.

Any of the beneficial agents may be administered in the form of a salt, ester, amide, prodrug, conjugate, active metabolite, isomer, fragment, analog, or the like, provided that the salt, ester, amide, prodrug, conjugate, active metabolite, isomer, fragment, or analog is pharmaceutically acceptable and pharmacologically active in the present context. Salts, esters, amides, prodrugs, conjugates, active metabolites, isomers, fragments, and analogs of the agents may be prepared using standard procedures known to those skilled in the art of synthetic organic chemistry and described, for example, by J. March, *Advanced Organic Chemistry: Reactions, Mechanisms and Structure,* 5th Edition (New York: Wiley-Interscience, 2001).

For example, acid addition salts are prepared from a drug in the form of a free base using conventional methodology involving reaction of the free base with an acid. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Conversely, preparation of basic salts of acid moieties that may be present on an active agent may be carried out in a similar manner using a pharmaceutically acceptable base such as sodium hydroxide, potassium hydroxide, ammonium hydroxide, calcium hydroxide, trimethylamine, or the like. Preparation of esters involves transformation of a carboxylic acid group via a conventional esterification reaction involving nucleophilic attack of an $RO^-$ moiety at the carbonyl carbon. Esterification may also be carried out by reaction of a hydroxyl group with an esterification reagent such as an acid chloride. Esters can be reconverted to the free acids, if desired, by using conventional hydrogenolysis or hydrolysis procedures. Amides may be prepared from esters, using suitable amine reactants, or they may be prepared from an anhydride or an acid chloride by reaction with ammonia or a lower alkyl amine. Prodrugs and active metabolites may also be prepared using techniques known to those skilled in the art or described in the pertinent literature. Prodrugs are typically prepared by covalent attachment of a moiety that results in a compound that is therapeutically inactive until modified by an individual's metabolic system.

Other derivatives and analogs of the active agents may be prepared using standard techniques known to those skilled in the art of synthetic organic chemistry, or may be deduced by reference to the pertinent literature. In addition, chiral active agents may be in isomerically pure form, or they may be administered as a racemic mixture of isomers.

The amount of the beneficial agent(s) in the formulation typically ranges from about 0.05 wt % to about 80 wt % based on the total weight of the formulation, preferably from about 0.1 wt % to about 50 wt %. The amount of beneficial agent in the formulation is an important factor in determining the amount of beneficial agent that is delivered to the mucous membrane of the patient. One of skill in the art will appreciate that dosages may vary depending on a variety of factors, including frequency of administration and the physical characteristics of the patient.

E. Optional Additives

In addition to the foregoing components, it may be necessary or desirable in some cases (depending, for instance, on the particular beneficial agent) to incorporate any of a variety of additives, e.g., components that improve bioadhesivity, drug delivery, shelf-life and patient acceptance. Suitable additives include without limitation acids, antioxidants, antimicrobials, buffers, crystal growth inhibitors, defoaming agents, diluents, emollients, fillers, gelling agents, fragrances, lubricants, propellants, thickeners, salts, solvents, surfactants, other chemical stabilizers, or mixtures thereof. Examples of these additives can be found, for example, in M. Ash and I. Ash, *Handbook of Pharmaceutical Additives* (Hampshire, England: Gower Publishing, 1995), the contents of which are herein incorporated by reference.

Additionally, adjuvants may be added to the formulations in order to enhance the immune system response, and are particularly desirable in the transmucosal delivery of vaccines. Suitable adjuvants may be selected from any of the adjuvants commonly known in the art. This includes, by way of example and not limitation, aluminum salts such as aluminum hydroxide and aluminum phosphate, dihydroepiandrosterone sulfate or 16α-bromo-dihydroepiandrosterone sulfate, cholera toxin, Freund's Complete Adjuvant, Freund's Incomplete Adjuvant, Montanide Incomplete Seppic Adjuvant, nitrocellulose-absorbed protein, γ-inulin, algammulin, and derivatives thereof.

Polymers may be added that affect the sustained release characteristics of the formulations. An example of such a polymer is polyethylene oxide.

F. Conditions Suitable for Treatment

Application of the formulations of the invention to the nasal mucous membrane allows for delivery of beneficial agents to a number of anatomical systems, including without limitation the central nervous system (CNS), respiratory system, lymphatic system and circulatory system. Similarly, application of the formulations of the invention to the vaginal and penile mucous membranes allows for delivery of beneficial agents to, for example, the reproductive and excretory systems. Application of the formulations of the invention to the oral mucous membranes allows for delivery of beneficial agents to, for example, the respiratory system. Accordingly, the formulations of the invention can be used in the prophylactic or therapeutic treatment of any systemic or localized conditions that effect these and related anatomical systems.

Conditions for which the formulations of the invention provide prophylactic or therapeutic treatment include, by way of example and not limitation, diseases and infections caused by fungi, viruses, bacteria, protozoa and the like, diseases and conditions characterized by inflammation, pain, neoplasms, impaired memory, impaired immune response, impaired or excessive appetite, sexual dysfunction, impaired or excessive sleep, psychological disorders or psychoses, and hormonal deficiencies or imbalances.

Specific examples of conditions for which the formulations of the invention provide prophylactic or therapeutic treatment include, by way of example and not limitation, Jacob Creutzfeldt disease, Parkinson's disease, cancer (including, for example, cancer of the thyroid, lungs, stomach, bladder, skin, mucousal tissue, colon, prostate, testis, cervix, and ovaries), Hodgkin's disease, and leukemia.

The formulations of the invention can also be used in the delivery of beneficial agents to the mucous membranes of the sexual organs. In this way the formulations of the invention can be used in the administration of contraceptives and beneficial agents designed to enhance or regulate sexual behavior.

III. Formulation Characteristics

At physiological temperatures (i.e., around 37° C.), the formulations of the invention are preferably viscous gels. Preferred viscosities are in the range of about 60,000 centipoise to about 250,000 centipoise. In addition, the formulations of the invention are preferably bioadhesive, such that they are able to adhere to biological surfaces such as mucous membranes. Bioadhesion results from, among other factors, the ability of the pH-responsive compound to adhere to biological surfaces. Preferably, sufficient amounts of the formulations remain attached to the mucous membranes for a length of time that allows an effective amount of the beneficial agent to be delivered to the patient. Without wishing to be bound by theory, the residency time of the formulation in the body is influenced by the amount of crosslinking (chemical or otherwise) that is present in the components of the formulation, as well as the strength of bioadhesive interactions between the formulation and the mucous membrane. Typically it is desired that the formulation is able to deliver a controlled release of beneficial agent over a period of between about 4 hours and about 24 hours, preferably at least about 4 hours, more preferably at least about 6 hours, most preferably 12 or more hours.

Prior to application to the mucous membrane, and at ambient temperature (i.e., around 25° C.), the formulations of the invention preferably have viscosities in the range of about 40,000 centipoise to about 300,000 centipoise. Again, without wishing to be bound by theory, the viscosity of the formulations under these conditions results from an interaction between the pH-responsive component and the temperature-responsive component. The pH of the formulation is sufficient to cause significant gelation of the pH-responsive component, thereby increasing the viscosity. However, at ambient temperatures, the temperature-responsive component is commonly water-soluble, and interferes with the ability of the pH-responsive component to form a gel. In addition, the formulations under these conditions typically exhibit shear thinning, and are thus able to be aerosolized via nebulizing drug delivery devices that are well-known in the art.

IV. Methods of Administration

The formulations of the invention are applied to a mucous membrane as a means of administering a beneficial agent to a patient. In general, the formulation that is applied directly to the mucous membrane comprises a pH-responsive compound and a temperature-responsive compound that in an aqueous medium is capable of undergoing a temperature-responsive sol to gel phase transition. The formulation may further comprise one or more of the following: beneficial agents; bases; water; excipients.

Mucous membranes that provide suitable locations for application include those in the oral, nasal, vaginal, penile or rectal cavities. The appropriate location for application varies depending upon a variety of factors. Examples of these factors include the identity and stability of the beneficial agent to be delivered, the duration and frequency of administration, and the desirability of controlled release of the beneficial agent.

The formulations of the invention are applied to the mucous membrane in the form of an aerosolized or bulk liquid. Means of application can be chosen from any of the common means known to those of ordinary skill in the art. Thus, any device, such as a nebulizer or spray bottle, that is capable of administering an aerosol of a liquid formulation to a mucous membrane may be used. In addition, any device such as a syringe, bottle, or applicator that is capable of administering a bulk liquid formulation to a mucous membrane may be used.

Homogenous distribution of the formulation components is preferably ensured prior to application. Prior to application, the components may be stored separately or in any combination that does not adversely effect application of the formulation, being combined shortly before application. Thus, for example, the pH-responsive component might be stored separately from any base that is to be included in the formulation, with the components being mixed prior to application. The beneficial agent may be stored in any manner (i.e., combined or not combined with any of the other components) that preserves its biological activity. For example, for temperature-sensitive beneficial agents, the beneficial agent may be stored below ambient temperatures, and mixed with the other formulation components prior to application. Preferably, the formulation is stored as two or more separate aqueous solutions. A first solution would contain at least the pH-responsive compound, and may optionally contain one or more beneficial agent and/or one or more excipients. The second solution would contain at least the temperature-responsive compound, and may optionally contain one or more of the following: bases, beneficial agents, excipients, or combinations thereof. Optionally, one or more beneficial agents may be stored with one or more excipients in a third solution. In a preferred embodiment, the formulation is stored as two solutions: a first solution containing the pH-responsive compound and any beneficial agents, and a second solution containing the temperature-responsive compound and any bases.

When stored as separate solutions, the formulation components must be mixed prior to application. Mixing of the components may be accomplished by any means that is sufficient to ensure that the beneficial agent is distributed with adequate uniformity throughout the mixture. When the formulation is stored as two separate solutions, a particularly preferred method of preparing (i.e., mixing) and administering the formulation is an applicator comprising two syringes, wherein the applicator further comprises a mixing nozzle in which the contents of the two syringes are mixed prior to being expelled from the applicator. By modifying the diameter of the applicator's orifice, the mixed formulation can be expelled from the applicator as either an aerosol or a bulk liquid. An example of an applicator that can be used for administration of the formulations of the invention is shown in FIG. 1.

For formulations applied in the form of aerosols, the extent of mixing of the formulation prior to application is preferably sufficient to provide a viscosity of between about 20,000 centipoise and about 300,000 centipoise, more preferably between about 30,000 centipoise and about 200,000 centipoise. This provides for a formulation that is viscous enough to efficiently adhere to the mucous membrane, but not so viscous as to make aerosolization difficult. Preferably, for application of the formulation using the double-syringe applicator that is described above, the mixing nozzle is of sufficient length and geometry to allow for the appropriate extent of mixing of the formulation components.

V. Kit

The formulations of the invention can be supplied to the patient in the form of single-dose kits or multiple-dose kits. Each kit shall comprise a pharmaceutical formulation and a means for delivery of the pharmaceutical formulation. The pharmaceutical formulation is any of the pharmaceutical formulations described herein, and shall comprise a pH-responsive compound and a temperature-responsive compound that in an aqueous medium is capable of undergoing a temperature-responsive sol to gel phase transition. The pharmaceutical formulation may furthermore comprise one or more beneficial agents, bases, water, excipients or combinations thereof. Depending upon the beneficial agents that are included in the formulation, the kit may be either for prophylactic or therapeutic use. Suitable beneficial agents include any of those described herein, such that the kit is useful in prophylactic use or therapeutic treatment against any of the conditions described herein.

VI. Utility

The formulations and methods of the invention can be useful in the area of transmucosal administration of beneficial agents. The formulations, which can be administered by a variety of methods, may exhibit bioadhesive properties. Such properties allow the formulations to remain in contact with mucous membranes for a period of time sufficient to allow delivery of a pharmaceutically effective amount of a beneficial agent. When appropriate, the formulations are also designed to elicit an enhanced immune response, thereby improving the efficacy of beneficial agent such as vaccines and antigens. An example of a particularly utility of the invention is the administration of Anthrax Vaccine Adsorbed. The formulations and methods of the invention are effective and simple when compared with traditional methods of administering AVA.

EXPERIMENTAL

The following materials were used in the formulations described in the examples: CARBOPOL® and polycarbophil NOVEON® AA-1 (obtained from Noveon); PLURONIC® F68, F108, F127, and L44 (obtained from BASF). Viscosities were measured using a Model DV-II+ Viscometer, Brookfield Engineering Labs, Middleboro, MA. Viscosity measurements were made at ambient and physiological temperatures. About two grams of a gel is placed into the spindle of the viseometer, which had been auto-zeroed. The spindle is staffed in motion, and viscosity readings are obtained. The spindle rpm is maintained at a desired level so as to obtain an equivalent % torque ranging from 10% to 100% for any combination of spindle and rotational speed.

Characteristic properties such as molecular weight and composition of polycarbophil and the various grades of PLURONICS® can be obtained from the respective manufacturer.

Example 1

Preparation of pH-Responsive Polymer and Temperature-Responsive Polymer Mixture Preparation Method A. A beaker with 100 ml of water was placed under a stirrer and mixing begun at 800-1200 rpm. The polymer (1 g of CARBOPOL® or 2 g of polycarbophil) was carefully added to the water and stirring continued for 15 mm to assure complete dispersion. The dispersion was then allowed to equilibrate for 30 mm without stirring. The mixer speed was reduced to 300 rpm and, while stirring, the neutralizing reagent was added. Addition of neutralizer was continued until the desired pH was reached.

Preparation Method B. A 50-ml aliquot of solution was warmed to 40° C., and 2 g of PLURONIC® F 127 was added. After stirring the solution at 200 rpm for 10 min, 50 ml of cold water was added and the mixture stirred for another 20 min till a clear solution is obtained. The clear solution was divided into two equivalent parts (Portion 1 and Portion 2, 50 ml each). To Portion 1 (50 ml of 2% of PLURONIC® by weight) added 2 g of polycarbophil, and the mixture was stirred for 10 mm. The mixture was neutralized, and left overnight at ambient temperature. Viscosity of the gel was measured, on both the days. The next day, when the Portion 1 semi-gel mixture was warmed to 37° C., a sudden change from sol to gel form was observed. The remaining solution (Portion 2) was used as a control. To Portion 2 (50 ml of 2% PLURONIC® by weight) added 2 g of PLURONIC® F127 and stirred to achieve complete dissolution. On raising temperature to 37° C., this control did not undergo any phase transition.

Table 1 lists the characteristics of the gel after neutralization. CARBOPOL® /polyearbophil at 1-2 wt % formed a high-viscosity gel (80,000 centipoise). Neither of these two gels demonstrated any change in gel form when the temperature was raised to 37° C.

A visual phase transition was observed on warming a mixture containing 2 wt % PLURONIC® +2 wt % polycarbophil. The resulting gel was sticky and more viscous than observed at ambient temperature. The resulting gel was both adhesive as well as cohesive. A control solution containing 4 wt % PLURONIC® F127 maintained its free-flowing form at both temperatures.

Example 3

Effect of Temperature on the Gel Viscosity of Polycarbophil

Procedure: See Example 1 for formulation preparation method. Data for a formulation consisting of 2 wt % polycarbophil is shown in Table 3. The viscosity was measured at ambient and the physiological temperature. In the latter case, the gel was maintained in the viscometer jacket at 37° C. for 30 minutes before measuring viscosity at the specified torque.

TABLE 1

Characteristics of Gels Obtained after Neutralization

| Entry | Formulation | Prep Method | First pH[a] | Second pH[b] | Viscosity of Gel | Observations Gel Raised to 37° C. |
|---|---|---|---|---|---|---|
| 1 | 1 wt % Carbopol | A | 3.4 | 5.0 | 72,796 cp at 1 RPM, 74.4% torque at 24.9° C. | No change |
| 2 | 2 wt % polycarbophil | A | 3.5 | 5.2 | 80,000 cp at 1 RPM, 80% torque at 25° C. | No change |
| 3 | 2 wt % polycarbophil + 2 wt % Pluronic® F127 | B, Portion 1 | NM[c] | NM | 10020 cp[d] at 1 RPM, 24% torque at 25° C. | Phase change formed highly adhesive gel |
| 4 | 4 wt % Pluronic® F127 | B, Portion 2 | NM | NM | Free solution | Free solution |

[a]Prior to neutralization.
[b]After neutralization.
[c]NM = not measured.
[d]Viscosity on Day 1

Example 2

Effect of Molecular Weight of Pluronics®

Method: The pH of an aqueous solution of PLURONICS® is measured. Subsequently, Polycarbophil is added to the solution, and the pH is measured again. Solutions are neutralized by adding sufficient amounts of aqueous NaOH to reach a pH of about 5, The viscosity of the resulting mixture is measured at 37° C., at different torques (Brookfield viscometer). Data is presented in Table 2.

TABLE 3

Gel Viscosity: Temperature Dependence

| | | Viscosit [cp] | | | |
|---|---|---|---|---|---|
| Entry | Temperature | 0.3 rpm | 0.6 rpm | 1.5 rpm | 3 rpm |
| 1 | room temperature | 152,000 | 84,100 | 38,500 | 22,000 |
| 2 | 37° C. | 245,000 | 128,000 | 55,000 | 30,000 |

TABLE 2

Pluronics® Grade vs. Viscosity of the Polycarbophil-Pluronic® Blend

| | | Viscosity [cp][1] | | | | | | |
|---|---|---|---|---|---|---|---|---|
| Entry | Formulation | 0.3 rpm | 0.6 rpm | 1.5 rpm | 3 rpm | pH before[2] | pH after[3] | Final pH[4] |
| 1 | 2 wt % PC[5] (control) | 245,000 | 128,000 | 55,000 | 30,000 | 3.5 | 3.59 | 5.16 |
| 2 | 2 wt % PC, 2 wt % Pluronic® F 127 | 183,000 | 92,000 | 40,000 | 22,800 | 6.79 | 3.58 | 55 |
| 3 | 2 wt % PC, 2 wt % Pluronic® F 108 | 193,000 | 107,000 | 44,000 | 25,000 | 4.9 | 3.58 | 5.09 |
| 4 | 2 wt % PC 2 wt % Pluronic® L 44 | 246,000 | 108,000 | 50,000 | 26,000 | 4.84 | 3.43 | 5.5 |
| 5 | 2 wt % PC 2 wt % Pluronic® F 68 | 237,000 | 125,000 | 54,556 | 30,200 | 6.22 | 3.51 | 5.15 |

[1]Viscosity measurements performed at 37° C.
[2]pH of the Pluronic® solution before addition of polycarbophil
[3]pH of the polymer solution after addition of polycarbophil
[4]Final pH after neutralization
[5]PC = Polycarbophil

Example 4

Effect of Formulation Composition

Procedure: See Example 1 for formulation preparation method. As shown in Table 4, increasing the weight percent of the polymers in the blend from 4% (entries 1b-5b) to 8% (entries 1a-5a) yielded an increase the viscosity of the gels. The trends observed in 4% polymer gels were maintained in 8% polymer gels. Decreasing critical micelle concentration of the PLURONICS® (relative CMC values: L44>F68>F108=F127) resulted in a corresponding decrease in viscosity.

TABLE 4

Viscosity vs. Gel Composition.

| Entry | Gel Composition | Viscosity [cp][a] |
|---|---|---|
| 1a | 4% polycarbophil (PC) | 320,000 |
| 2a | 4 wt % PC, 4 wt % Pluronics ® F 127 | 281,000 |
| 3a | 4 wt % PC, 4 wt % Pluronics ® F 68 | 294,000 |
| 4a | 4 wt % PC, 4 wt % Pluronics ® L 44 | 305,000 |
| 5a | 4 wt % PC 4 wt % Pluronics ® F 108 | 330,000 |
| 1b | 2% polycarbophil (PC) | 245,000 |
| 2b | 2 wt % PC, 2 wt % Pluronics ® F 127 | 183,000 |
| 3b | 2 wt % PC, 2 wt % Pluronics ® F 68 | 237,000 |
| 4b | 2 wt % PC, 2 wt % Pluronics ® L 44 | 246,000 |
| 5b | 2 wt % PC 2 wt % Pluronics ® F 108 | 193,000 |

[a]Viscosities measured at 0.3 rpm and 37° C.

Example 5

Higher Concentration of Pluronics®

Procedure: See Example 1 for formulation preparation method. Table 5 shows gelation behavior at various temperatures for formulations comprising at least 10 wt % PLURONIC® F127.

Example 6

Formulation Preparation and Testing: 0.5 wt % BSA

In order to demonstrate the ability of molecules of relatively high molecular weight to diffuse out of the gel formulations disclosed herein, gel samples were prepared using Bovine Serum Albumin (BSA, molecular weight=66,000 g mol$^{-1}$) as the beneficial agent.

Figure 2:
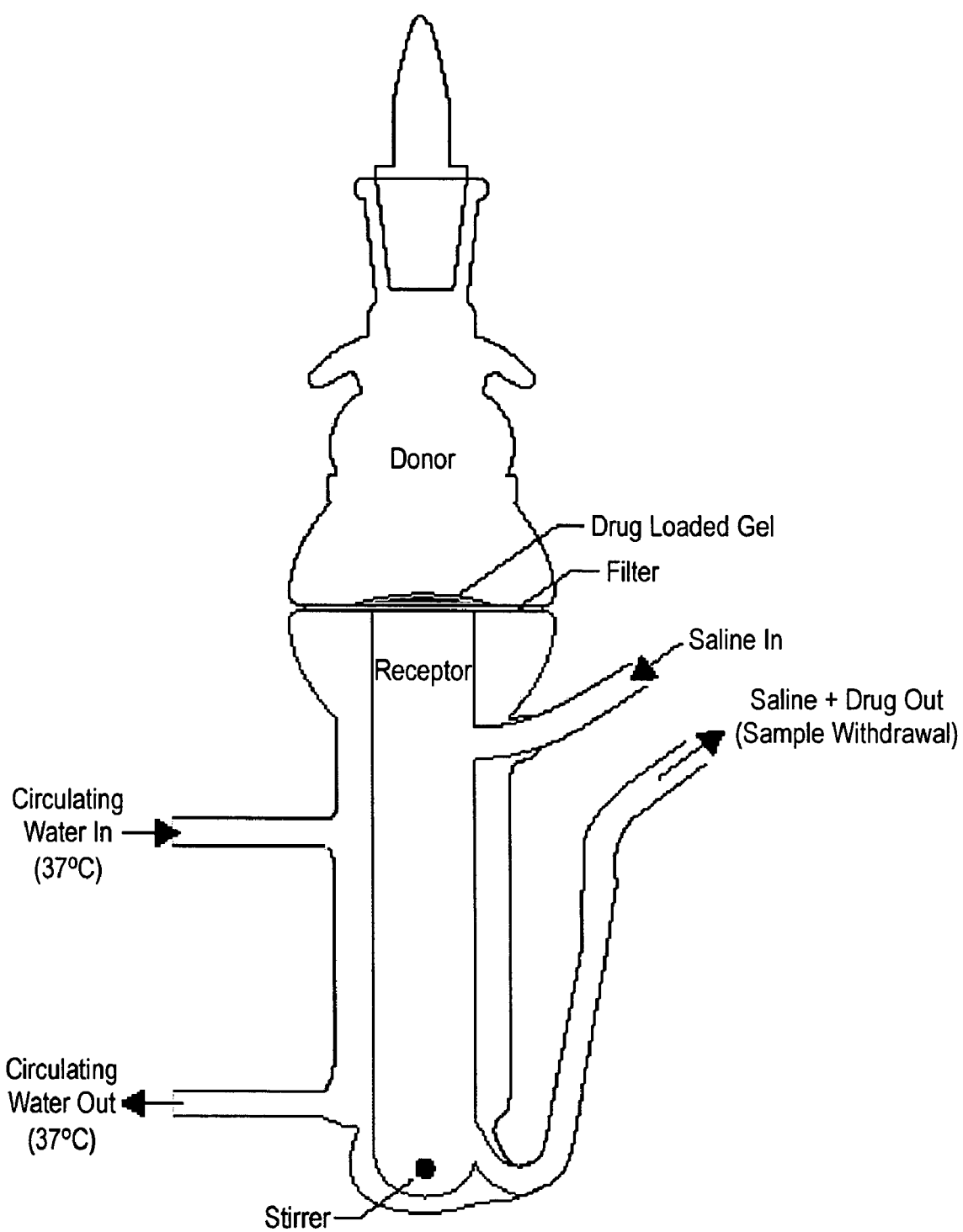
FIG. 2 is a diagram of the Franz-cell apparatus suitable for measuring release of beneficial agent from the formulations of the invention.

A representative example of the method of preparation for the formulations is as follows: To prepare formulation A, containing 0.25 wt % PLURONIC® F127 and 0.25 wt % polycarbophil, 37.5 mg of polycarbophil was added to 12.5 mL of 0.3 wt % aqueous PLURONIC® F127 solution. The mixture was stirred at 1,200 rpm for 15 min. Subsequently, 75 mg of BSA in 2.5 mL deionized water solution was added, and the mixture was stirred at 12000 rpm for 5 min. The mixture was neutralized by adding 1 M NaOH until a pH of 6 was obtained, and the mixture was centrifuged at 12,000 rpm for 8 min. A 0.5 mL aliquot of the polymer gel was removed and placed on top of a 0.45 μm filter. The filter was placed on a Franz cell between the donor and receptor compartments, as shown in FIG. 2. To the donor compartment was added 2.0 mL of 1x Phosphate Buffered Saline (PBS). Additional 1x PBS was pumped through the cell at a rate of 5 mL/min. The receiver compartment was maintained at 37 ° C. Liquid samples were collected from the receiver at specific time intervals and UV absorbance at 280 nm was measured, thus allowing determination of the amount of released BSA.

Formulations B, containing 0.50 wt % PLURONIC® F127 and 0.50 wt % polycarbophil, and formulation C, containing 2.0 wt % PLURONIC® F127 and 2.0 wt % polycarbophil, were prepared similarly to formulation A.

Duplicate release samples were set up for each weight percent of gel/BSA combination. Samples were analyzed on Franz cells. Each of the gels had 0.5% BSA loading.

Figure 3:
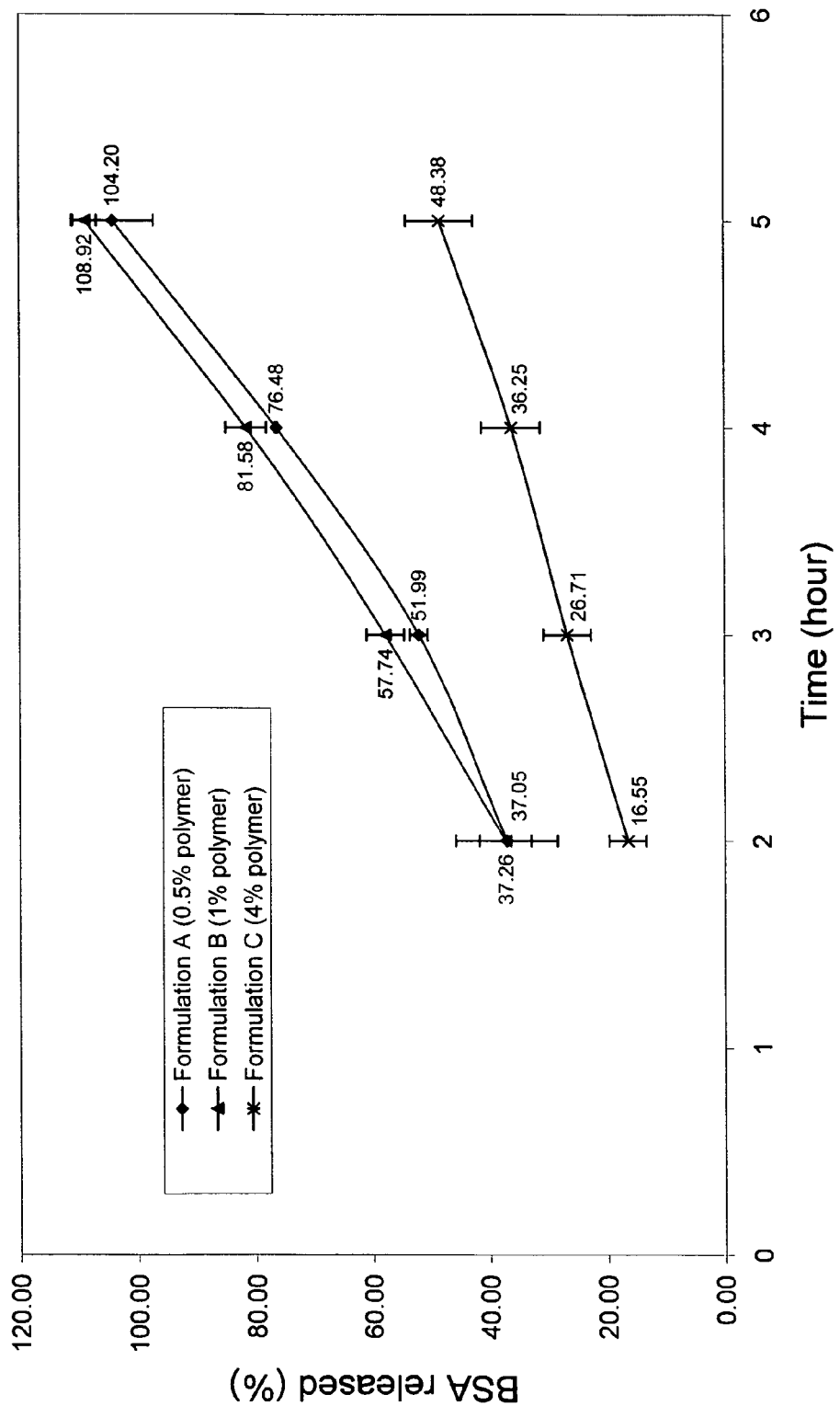
FIG. 3 is a graph displaying the percentage of Bovine Serum Albumin released into phosphate buffered solution from gels of different composition.

As shown in FIG. 3, the polymeric gel from formulation A showed faster release of BSA and greater standard deviation (as seen by the error bars) as compared with formulation C.

TABLE 5

Gelation Behavior vs. Composition

| Entry | Wt % of Pluronic ® F127 | Wt % of Polycarbophil | Phase of Polycarbophil added | Gel at 4° C. | Gel at room temperature | Gel 37° C. | Gel rating[a] |
|---|---|---|---|---|---|---|---|
| 1 | 30 | 0 | N/A | No | Slowly (pH 7.33) | very easily | 4 |
| 2 | 30 | 2 | solid | No | Slowly (pH 4.44) | very easily | 3 |
| 3 | 10 | 1 | liquid | N/A | No (pH 3.37) | No | 1[b] |
| 4 | 20 | 2 | solid | N/A | Slowly (pH 6.54) | easily | 3 |

[a]Subjective rating of gel viscosity: 4 = strong gel, 1 = weak gel.
[b]Increasing pH and temperature did not cause gelling.

Similarly, formulation B showed faster release of BSA and a greater standard deviation as compared with formulation C.

Example 7

Formulation Preparation and Testing: 0.5 wt % Caffeine

In order to demonstrate the ability of molecules of relatively low molecular weight to diffuse out of the gel formulations disclosed herein, gel samples were prepared using caffeine (molecular weight=194 g mol$^{-1}$) as the beneficial agent. The procedure of Example 6 was followed in preparing three formulations (A, B and C), each containing 0.5 wt % caffeine.

As shown in FIG. 4, the polymeric gel from formulation A showed faster release of caffeine and greater standard deviation (as seen by the error bars) as compared with formulation C. Similarly, formulation B also showed faster release of caffeine and greater standard deviation as compared with formulation C.

The invention claimed is:

1. A bioadhesive aqueous pharmaceutical formulation for controlled, transmucosal delivery of a beneficial agent, comprising:
   (a) from 0.5 wt % to no more than 5 wt % total pH-responsive polycarbophils, wherein the polycarbophils exhibit base-dependent bioadhesiveness;
   (b) from 0.5 wt % to no more than 5 wt % total temperature-responsive alkylene oxide copolymers, wherein the alkylene oxide copolymers exhibits reverse thermal gelation;
   (c) a base in an amount sufficient for the pH of the formulation to be in the range of about 5 to about 7, thereby imparting bioadhesiveness of the pH-responsive polycarbophils; and
   (d) an effective amount of a beneficial agent;
   wherein the formulation has a sol-gel phase transition temperature between about 30° C. and about 40° C., is bioadhesive, and provides controlled, transmucosal delivery of the beneficial agent.

2. The pharmaceutical formulation of claim 1, wherein the pH-responsive is polycarbophils are sold under the registered trademark NOVEON®.

3. The pharmaceutical formulation of claim 1, wherein the pH-responsive polycarbophils are is sold under the registered trademark NOVEON AA-1®.

4. The pharmaceutical formulation of claim 1, wherein the temperature-responsive alkylene oxide copolymers are is sold under the registered trademark PLURONIC®.

5. The pharmaceutical formulation of claim 1, wherein the temperature-responsive alkylene oxide copolymers are sold under the registered trademark PLURONIC® and is selected from the group consisting of PLURONIC F 127®, PLURONIC F 108®, PLURONIC L 44®, and PLURONIC F 68®.

6. The pharmaceutical formulation of claim 1, wherein the temperature-responsive alkylene oxide copolymers are sold under the registered trademark PLURONIC F 127®.

7. The pharmaceutical formulation of claim 1, wherein the sum of the weight percent of the pH-responsive polycarbophils and the weight percent of the temperature-responsive alkylene oxide copolymers is in the range of 1% to 5%.

8. The pharmaceutical formulation of claim 1, wherein the sum of the weight percent of the pH-responsive polycarbophils and the weight percent of the temperature-responsive alkylene oxide copolymers is 4%.

9. The pharmaceutical formulation of claim 1, wherein the weight of the pH-responsive polycarbophils is in the range of 1% to 2% of the total weight of the formulation.

10. The pharmaceutical formulation of claim 1, wherein the weight of the temperature-responsive alkylene oxide copolymers is in the range of 1% to 2% of the total weight of the formulation.

11. The pharmaceutical formulation of claim 1, wherein the beneficial agent is selected from the group consisting of antigens, anti-allergy agents, antibiotics, antivirals, anti-inflammatories, steroids, antineoplastics, anesthetics, enzymes, genetic material, viral vectors, immunoactive agents, vaccines, immunosuppressive agents, peptides, proteins, and combinations thereof.

12. The pharmaceutical formulation of claim 1, wherein the beneficial agent comprises an antigen or vaccine.

13. The pharmaceutical formulation of claim 1, wherein the beneficial agent comprises a vaccine effective to reduce the likelihood of anthrax.

14. The pharmaceutical formulation of claim 1, wherein the beneficial agent comprises Anthrax Vaccine Adsorbed.

15. The pharmaceutical formulation of claim 1, wherein the formulation further comprises an adjuvant.

16. The pharmaceutical formulation of claim 1, wherein the base is selected from sodium hydroxide, potassium hydroxide, ammonium hydroxide, triethanol amine, aminomethyl propanol, 2-amino-2-hydroxymethyl-1,3-propanediol, and tetrahydroxypropyl ethylenediamine.

17. The pharmaceutical formulation of claim 1, wherein the formulation has a gel viscosity greater than about 50,000 centipoise as measured on a Brookfield viscometer at 37° C. and at a spindle speed of 0.6 rpm.

18. The pharmaceutical formulation of claim 1, wherein:
   the pH-responsive polycarbophils are sold under the registered trademark NOVEON AA-1®;
   the temperature-responsive alkylene oxide copolymers is sold under the registered trademark PLURONIC F 127®;
   the base is selected from sodium hydroxide, potassium hydroxide, ammonium hydroxide, triethanol amine, aminomethyl propanol, 2-amino-2-hydroxymethyl-1,3-propanediol, and tetrahydroxypropyl ethylenediamine; and
   the formulation has a gel viscosity greater than about 50,000 centipoise as measured on a Brookfield viscometer at 37° C. and at a spindle speed of 0.6 rpm.

19. A method for treating a patient suffering from a bacterial infection, comprising administering to the patient a therapeutically effective amount of a bioadhesive pharmaceutical formulation according to claim 1 wherein the pharmaceutical formulation is administered via application to a mucous membrane.

20. The method of claim 19, wherein the pharmaceutical formulation forms a gel upon application to the mucous membrane, wherein the gel has a viscosity greater than 40,000 centipoise as measured on a Brookfield viscometer at 37° C. and at a spindle speed of 0.6 rpm.

21. The method of claim 19, wherein the effective amount of the pharmaceutical formulation remains in contact with the mucous membrane for a period of time of at least 4 hours.

22. The method of claim 19, wherein:
   the pH-responsive polycarbophils are sold under the registered trademark NOVEON AA-1®;
   the temperature-responsive alkylene oxide copolymers are sold under the registered trademark PLURONIC F 127®;

the base is selected from sodium hydroxide, potassium hydroxide, ammonium hydroxide, triethanol amine, aminomethyl propanol, 2-amino-2-hydroxymethyl-1,3-propanediol, and tetrahydroxypropyl ethylenediamine; and the formulation has a gel viscosity greater than about 50,000 centipoise as measured on a Brookfield viscometer at 37° C. and at a spindle speed of 0.6 rpm.

23. A method for decreasing the likelihood of a bacterial infection in a patient, comprising administering to the patient an effective amount of a bioadhesive pharmaceutical formulation according to claim 1, wherein the pharmaceutical formulation is administered via application to a mucous membrane.

24. The method of claim 23, wherein the beneficial agent comprises a vaccine effective in reducing the likelihood of anthrax.

25. The method of claim 23, wherein the beneficial agent comprises Anthrax Vaccine Adsorbed.

26. The method of claim 23, wherein the pharmaceutical formulation forms a gel upon application to the mucous membrane, wherein the gel has a viscosity above about 40,000 centipoise as measured on a Brookfield viscometer at 37° C. and a spindle speed of about 0.6 rpm.

27. The method of claim 23, wherein the effective amount of the pharmaceutical formulation remains in contact with the mucous membrane for a period of time of at least 4 hours.

28. The method of claim 23, wherein:
the pH-responsive polycarbophils are sold under the registered trademark NOVEON AA-1®;
the temperature-responsive alkylene oxide copolymers are sold under the registered trademark PLURONIC F 127®;
the base is selected from sodium hydroxide, potassium hydroxide, ammonium hydroxide, triethanol amine, aminomethyl propanol, 2-amino-2-hydroxymethyl-1,3-propanediol, and tetrahydroxypropyl ethylenediamine; and
the formulation has a gel viscosity greater than about 50,000 centipoise as measured on a Brookfield viscometer at 37° C. and at a spindle speed of 0.6 rpm.

29. A method for administering a beneficial agent to a mucous membrane of a patient, comprising applying to the mucous membrane a bioadhesive pharmaceutical formulation according to claim 1.

30. The method of claim 29, further comprising mixing the polycarbophils and the alkylene oxide copolymers prior to applying them to the mucous membrane.

31. The method of claim 29, further comprising mixing the beneficial agent with the pH-responsive polycarbophils prior to mixing the pH-responsive polycarbophils and the temperature-responsive alkylene oxide copolymers.

32. The method of claim 29, further comprising mixing the pH-responsive polycarbophils and the temperature-responsive alkylene oxide copolymers prior to applying them to the mucous membrane, wherein the mixing occurs within an applicator.

33. The method of claim 29, wherein the viscosity of the formulation after mixing the pH-responsive polycarbophils and the temperature-responsive alkylene oxide copolymers is above 40,000 centipoise as measured on a Brookfield viscometer at 37° C. at a spindle speed of 0.6 rpm.

34. The method of claim 29, wherein the viscosity of the formulation after mixing the pH-responsive polycarbophils and the temperature-responsive alkylene oxide copolymers is greater than the viscosity of the pH-responsive polycarbophils before the mixing and greater than the viscosity of the temperature-responsive alkylene oxide copolymers before the mixing.

35. The method of claim 29, wherein the formulation is applied to the mucous membrane by means of a nebulizer, applicator or syringe.

36. The method of claim 29, wherein the mucous membrane is nasal.

37. The method of claim 29, wherein the beneficial agent is selected from an antigen, antibiotic, vaccine, or pharmaceutical.

38. The method of claim 29, wherein the beneficial agent comprises a vaccine.

39. The method of claim 38, wherein the vaccine is effective in reducing the likelihood of anthrax.

40. The method of claim 38, wherein the vaccine is Anthrax Vaccine Adsorbed.

41. The method of claim 29, wherein:
the pH-responsive polycarbophils are sold under the registered trademark NOVEON AA-1®;
the temperature-responsive alkylene oxide copolymers are sold under the registered trademark PLURONIC F 127®;
the base is selected from sodium hydroxide, potassium hydroxide, ammonium hydroxide, triethanol amine, aminomethyl propanol, 2-amino-2-hydroxymethyl-1,3-propanediol, and tetrahydroxypropyl ethylenediamine; and
the formulation has a gel viscosity greater than about 50,000 centipoise as measured on a Brookfield viscometer at 37° C. and at a spindle speed of 0.6 rpm.

42. A prophylactic kit for reducing the likelihood of disease caused by a bacterial infection in a patient comprising:
(a) a bioadhesive pharmaceutical formulation according to claim 1; and
(b) an applicator for delivery of the pharmaceutical formulation.

43. The prophylactic kit of claim 42, wherein the bacterial infection is caused by the bacterium *Bacillus anthracis*, and the beneficial agent comprises a vaccine effective in reducing the likelihood of anthrax.

44. The prophylactic kit of claim 42, wherein the applicator comprises a first syringe containing the pH-responsive polycarbophils and the beneficial agent, and a second syringe containing the temperature-responsive alkylene oxide copolymers and the base.

45. The prophylactic kit of claim 42, wherein the applicator comprises a first syringe containing the pH-responsive polycarbophils and the beneficial agent, and a second syringe containing the temperature-responsive alkylene oxide copolymers and the base, wherein the applicator further comprises a mixing nozzle that allows the contents of the first syringe to be mixed with the contents of the second syringe prior to application.

46. The prophylactic kit of claim 42, wherein:
the pH-responsive polycarbophils are sold under the registered trademark NOVEON AA-1®;
the temperature-responsive alkylene oxide copolymers are sold under the registered trademark PLURONIC F 127®;
the base is selected from sodium hydroxide, potassium hydroxide, ammonium hydroxide, triethanol amine, aminomethyl propanol, 2-amino-2-hydroxymethyl-1,3-propanediol, and tetrahydroxypropyl ethylenediamine; and the formulation has a gel viscosity greater than 50,000 centipoise as measured on a Brookfield viscometer at 37° C. and at a spindle speed of 0.6 rpm.

47. A therapeutic kit for treating disease caused by a bacterial infection in a patient comprising:
(a) a bioadhesive pharmaceutical formulation according to claim 1; and
(b) an applicator for delivery of the pharmaceutical formulation.

48. The therapeutic kit of claim 47, wherein the applicator comprises a first syringe containing the pH-responsive polycarbophils and the beneficial agent, and a second syringe containing the temperature-responsive alkylene oxide copolymers and the base.

49. The therapeutic kit of claim 47, wherein the applicator comprises a first syringe containing the pH-responsive polycarbophils and the beneficial agent, and a second syringe containing the temperature-responsive alkylene oxide copolymers and the base, wherein the applicator further comprises a mixing nozzle that allows the contents of the first syringe to be mixed with the contents of the second syringe prior to application.

50. The therapeutic kit of claim 47, wherein:
the pH-responsive polycarbophils are sold under the registered trademark NOVEON AA-1®;
the temperature-responsive alkylene oxide copolymers are sold under the registered trademark PLURONIC F 127®;
the base is selected from sodium hydroxide, potassium hydroxide, ammonium hydroxide, triethanol amine, aminomethyl propanol, 2-amino-2-hydroxymethyl-1,3-propanediol, and tetrahydroxypropyl ethylenediamine; and
the formulation has a gel viscosity greater than 50,000 centipoise as measured on a Brookfield viscometer at 37° C. and at a spindle speed of 0.6 rpm.

51. A bioadhesive aqueous pharmaceutical formulation for controlled, transmucosal delivery of a beneficial agent, comprising:
(a) from 1 wt % to no more than 2 wt % total pH-responsive polycarbophils, wherein the polycarbophils exhibit base-dependent bioadhesiveness;
(b) from 1 wt % to no more than 2 wt % total temperature-responsive alkylene oxide copolymers, wherein the alkylene oxide copolymers exhibit reverse thermal gelation;
(c) a base in an amount sufficient for the pH of the formulation to be in the range of about 5 to about 7, thereby imparting bioadhesiveness of the pH-responsive polycarbophils; and
(d) an effective amount of a beneficial agent;
wherein the formulation has a sol-gel phase transition temperature between about 30° C. and about 40° C., is bioadhesive, and provides controlled, transmucosal delivery of the beneficial agent.

52. The pharmaceutical formulation of claim 51, wherein the pH-responsive polycarbophils are sold under the registered trademark NOVEON®.

53. The pharmaceutical formulation of claim 51, wherein the pH-responsive polycarbophils are sold under the registered trademark NOVEON AA-1®.

54. The pharmaceutical formulation of claim 51, wherein the temperature-responsive alkylene oxide copolymers are sold under the registered trademark PLURONIC®.

55. The pharmaceutical formulation of claim 51, wherein the temperature-responsive alkylene oxide copolymers are sold under the registered trademark PLURONIC and is selected from the group consisting of PLURONIC F 127®, PLURONIC F 108®, PLURONIC L 44®, and PLURONIC F 68®.

56. The pharmaceutical formulation of claim 51, wherein the temperature-responsive alkylene oxide copolymers are sold under the registered trademark PLURONIC F 127®.

57. The pharmaceutical formulation of claim 51, wherein the sum of the weight percent of the pH-responsive polycarbophils and the weight percent of the temperature-responsive alkylene oxide copolymers is 2%.

58. The pharmaceutical formulation of claim 51, wherein the sum of the weight percent of the pH-responsive polycarbophils and the weight percent of the temperature-responsive alkylene oxide copolymers is 4%.

59. The pharmaceutical formulation of claim 51, wherein the weight of the pH-responsive polycarbophils is 2% of the total weight of the formulation.

60. The pharmaceutical formulation of claim 51, wherein the weight of the temperature-responsive alkylene oxide copolymers is 2% of the total weight of the formulation.

61. The pharmaceutical formulation of claim 51, wherein the beneficial agent is selected from the group consisting of antigens, anti-allergy agents, antibiotics, antivirals, anti-inflammatories, steroids, antineoplastics, anesthetics, enzymes, genetic material, viral vectors, immunoactive agents, vaccines, immunosuppressive agents, peptides, proteins, and combinations thereof.

62. The pharmaceutical formulation of claim 51, wherein the beneficial agent comprises an antigen or vaccine.

63. The pharmaceutical formulation of claim 51, wherein the beneficial agent comprises a vaccine effective to reduce the likelihood of anthrax.

64. The pharmaceutical formulation of claim 51, wherein the beneficial agent comprises Anthrax Vaccine Adsorbed.

65. The pharmaceutical formulation of claim 51, wherein the formulation further comprises an adjuvant.

66. The pharmaceutical formulation of claim 51, wherein the base is selected from sodium hydroxide, potassium hydroxide, ammonium hydroxide, triethanol amine, aminomethyl propanol, 2-amino-2-hydroxymethyl-1,3-propanediol, and tetrahydroxypropyl ethylenediamine.

67. The pharmaceutical formulation of claim 51, wherein the formulation has a gel viscosity greater than about 50,000 centipoise as measured on a Brookfield viscometer at 37° C. and at a spindle speed of 0.6 rpm.

68. The pharmaceutical formulation of claim 51, wherein:
the pH-responsive polycarbophils are sold under the registered trademark NOVEON AA-1®;
the temperature-responsive alkylene oxide copolymers are under the registered trademark PLURONIC F 127®;
the base is selected from sodium hydroxide, potassium hydroxide, ammonium hydroxide, triethanol amine, aminomethyl propanol, 2-amino-2-hydroxymethyl-1,3-propanediol, and tetrahydroxypropyl ethylenediamine; and
the formulation has a gel viscosity greater than about 50,000 centipoise as measured on a Brookfield viscometer at 37° C. and at a spindle speed of 0.6 rpm.

69. A method for treating a patient suffering from a bacterial infection, comprising administering to the patient a therapeutically effective amount of a bioadhesive pharmaceutical formulation according to claim 51 wherein the pharmaceutical formulation is administered via application to a mucous membrane.

70. The method of claim 69, wherein the pharmaceutical formulation forms a gel upon application to the mucous membrane, wherein the gel has a viscosity greater than 40,000 centipoise as measured on a Brookfield viscometer at 37° C. and at a spindle speed of 0.6 rpm.

71. The method of claim 69, wherein the effective amount of the pharmaceutical formulation remains in contact with the mucous membrane for a period of time of at least 4 hours.

72. The method of claim 69, wherein:
the pH-responsive polycarbophils are sold under the registered trademark NOVEON AA-1®;
the temperature-responsive alkylene oxide copolymers are under the registered trademark PLURONIC F 127®;
the base is selected from sodium hydroxide, potassium hydroxide, ammonium hydroxide, triethanol amine, aminomethyl propanol, 2-amino-2-hydroxymethyl-1,3-propanediol, and tetrahydroxypropyl ethylenediamine; and
the formulation has a gel viscosity greater than about 50,000 centipoise as measured on a Brookfield viscometer at 37° C. and at a spindle speed of 0.6 rpm.

73. A method for decreasing the likelihood of disease caused by a bacterial infection in a patient, comprising administering to the patient an effective amount of a bioadhesive pharmaceutical formulation according to claim 51, wherein the pharmaceutical formulation is administered via application to a mucous membrane.

74. The method of claim 73, wherein the beneficial agent comprises a vaccine effective in reducing the likelihood of anthrax.

75. The method of claim 73, wherein the beneficial agent comprises Anthrax Vaccine Adsorbed.

76. The method of claim 73, wherein the pharmaceutical formulation forms a gel upon application to the mucous membrane, wherein the gel has a viscosity above about 40,000 centipoise as measured on a Brookfield viscometer at 37° C. and a spindle speed of about 0.6 rpm.

77. The method of claim 73, wherein the effective amount of the pharmaceutical formulation remains in contact with the mucous membrane for a period of time of at least 4 hours.

78. The method of claim 73, wherein:

the pH-responsive polycarbophils are sold under the registered trademark NOVEON AA-1®;

the temperature-responsive alkylene oxide copolymers are sold under the registered trademark PLURONIC F 127®;

the base is selected from sodium hydroxide, potassium hydroxide, ammonium hydroxide, triethanol amine, aminomethyl propanol, 2-amino-2-hydroxymethyl-1,3-propanediol, and tetrahydroxypropyl ethylenediamine; and the formulation has a gel viscosity greater than about 50,000 centipoise as measured on a Brookfield viscometer at 37° C. and at a spindle speed of 0.6 rpm.

79. A method for administering a beneficial agent to a mucous membrane of a patient, comprising applying to the mucous membrane a bioadhesive pharmaceutical formulation according to claim 51.

80. The method of claim 79, further comprising mixing the polycarbophils and the alkylene oxide copolymers prior to applying them to the mucous membrane.

81. The method of claim 79, further comprising mixing the beneficial agent with the pH-responsive polycarbophils prior to mixing the pH-responsive polycarbophils and the temperature-responsive alkylene oxide copolymers.

82. The method of claim 79, further comprising mixing the pH-responsive polycarbophils and the temperature-responsive alkylene oxide copolymers prior to applying them to the mucous membrane, wherein the mixing occurs within an applicator.

83. The method of claim 79, wherein the viscosity of the formulation after mixing the pH-responsive polycarbophils and the temperature-responsive alkylene oxide copolymers is above 40,000 centipoise as measured on a Brookfield viscometer at 37° C. at a spindle speed of 0.6 rpm.

84. The method of claim 79, wherein the viscosity of the formulation after mixing the pH-responsive polycarbophils and the temperature-responsive alkylene oxide copolymers is greater than the viscosity of the pH-responsive polycarbophils before the mixing and greater than the viscosity of the temperature-responsive alkylene oxide copolymers before the mixing.

85. The method of claim 79, wherein the formulation is applied to the mucous membrane by means of a nebulizer, applicator or syringe.

86. The method of claim 79, wherein the mucous membrane is nasal.

87. The method of claim 79, wherein the beneficial agent is selected from an antigen, antibiotic, vaccine, or pharmaceutical.

88. The method of claim 79, wherein the beneficial agent comprises a vaccine.

89. The method of claim 88, wherein the vaccine is effective in reducing the likelihood of anthrax.

90. The method of claim 88, wherein the vaccine is Anthrax Vaccine Adsorbed.

91. The method of claim 79, wherein:

the pH-responsive polycarbophils are sold under the registered trademark NOVEON AA-1®;

the temperature-responsive alkylene oxide copolymers are under the registered trademark PLURONIC F 127®;

the base is selected from sodium hydroxide, potassium hydroxide, ammonium hydroxide, triethanol amine, aminomethyl propanol, 2-amino-2-hydroxymethyl-1,3-propanediol, and tetrahydroxypropyl ethylenediamine; and the formulation has a gel viscosity greater than about 50,000 centipoise as measured on a Brookfield viscometer at 37° C. and at a spindle speed of 0.6 rpm.

92. A prophylactic kit for reducing the likelihood of disease cause by a bacterial infection in a patient comprising:

(a) a bioadhesive pharmaceutical formulation according to claim 51; and (b) an applicator for delivery of the pharmaceutical formulation.

93. The prophylactic kit of claim 92, wherein the bacterial infection is caused by the bacterium *Bacillus anthracis*, and the beneficial agent comprises a vaccine effective in reducing the likelihood of anthrax.

94. The prophylactic kit of claim 92, wherein the applicator comprises a first syringe containing the pH-responsive polycarbophils and the beneficial agent, and a second syringe containing the temperature-responsive alkylene oxide copolymers and the base.

95. The prophylactic kit of claim 92, wherein the applicator comprises a first syringe containing the pH-responsive polycarbophils and the beneficial agent, and a second syringe containing the temperature-responsive alkylene oxide copolymers and the base, wherein the applicator further comprises a mixing nozzle that allows the contents of the first syringe to be mixed with the contents of the second syringe prior to application.

96. The prophylactic kit of claim 92, wherein:

the pH-responsive polycarbophils are sold under the registered trademark NOVEON AA-1®;

the temperature-responsive alkylene oxide copolymers are sold under the registered trademark PLURONIC F 127®;

the base is selected from sodium hydroxide, potassium hydroxide, ammonium hydroxide, triethanol amine, aminomethyl propanol, 2-amino-2-hydroxymethyl-1,3-propanediol, and tetrahydroxypropyl ethylenediamine; and the formulation has a gel viscosity greater than 50,000 centipoise as measured on a Brookfield viscometer at 37° C. and at a spindle speed of 0.6 rpm.

97. A therapeutic kit for treating disease caused by a bacterial infection in a patient comprising:

(a) a bioadhesive pharmaceutical formulation according to claim 51; and (b) an applicator for delivery of the pharmaceutical formulation.

98. The therapeutic kit of claim 97, wherein the applicator comprises a first syringe containing the pH-responsive polycarbophils and the beneficial agent, and a second syringe containing the temperature-responsive alkylene oxide copolymers and the base.

99. The therapeutic kit of claim 97, wherein the applicator comprises a first syringe containing the pH-responsive polycarbophils and the beneficial agent, and a second syringe containing the temperature-responsive alkylene oxide copolymers and the base, wherein the applicator further comprises a mixing nozzle that allows the contents of the first syringe to be mixed with the contents of the second syringe prior to application.

100. The therapeutic kit of claim 97, wherein:

the pH-responsive polycarbophils are sold under the registered trademark NOVEON AA-1®;

the temperature-responsive alkylene oxide copolymers are under the registered trademark PLURONIC F 127®;

the base is selected from sodium hydroxide, potassium hydroxide, ammonium hydroxide, triethanol amine, aminomethyl propanol, 2-amino-2-hydroxymethyl-1,3-propanediol, and tetrahydroxypropyl ethylenediamine; and the formulation has a gel viscosity greater than 50,000 centipoise as measured on a Brookfield viscometer at 37° C. and at a spindle speed of 0.6 rpm.

* * * * *